US007468194B1

(12) United States Patent
Fleischer et al.

(10) Patent No.: US 7,468,194 B1
(45) Date of Patent: Dec. 23, 2008

(54) PREPARATIONS FOR THE APPLICATION OF ANTI-INFLAMMATORY AGENTS

(75) Inventors: Wolfgang Fleischer, Ingelheim (DE); Karen Reimer, Hambach (DE)

(73) Assignee: Euro-Celtique, S.A., Luxembourg (LU)

( * ) Notice: Subject to any disclaimer, the term of this patent is extended or adjusted under 35 U.S.C. 154(b) by 0 days.

(21) Appl. No.: 09/979,852

(22) PCT Filed: May 25, 2000

(86) PCT No.: PCT/EP00/04783

§ 371 (c)(1),
(2), (4) Date: Nov. 27, 2001

(87) PCT Pub. No.: WO00/72823

PCT Pub. Date: Dec. 7, 2000

(30) Foreign Application Priority Data

May 27, 1999 (DE) ................................. 199 24 313

(51) Int. Cl.
*A61K 9/127* (2006.01)
*A61K 9/36* (2006.01)
*A61K 31/74* (2006.01)
*A61K 31/79* (2006.01)
*A61K 25/00* (2006.01)

(52) U.S. Cl. .................... 424/450; 424/480; 424/78.07; 424/78.24; 424/405; 424/417

(58) Field of Classification Search ................. 424/480, 424/78.04, 78.07, 78.24, 405, 417, 450
See application file for complete search history.

(56) References Cited

U.S. PATENT DOCUMENTS

| | | | |
|---|---|---|---|
| 2,706,701 A | 4/1955 | Beller et al. | 167/70 |
| 4,113,857 A | 9/1978 | Shetty | 424/150 |
| 4,235,871 A | 11/1980 | Papahadjopoulous et al. | 424/19 |
| 4,560,678 A | 12/1985 | Ranson | 514/44 |
| 4,675,009 A | 6/1987 | Hymes et al. | 604/304 |
| 4,906,476 A | 3/1990 | Radhakrishnan | 424/450 |
| 4,938,965 A | 7/1990 | Shek et al. | 424/450 |
| 5,034,228 A | 7/1991 | Meybeck et al. | 424/401 |
| 5,049,388 A | 9/1991 | Knight et al. | 424/450 |
| 5,049,389 A | 9/1991 | Radhakrishnan | 424/450 |
| 5,114,928 A | 5/1992 | Gajdos et al. | 514/25 |
| 5,128,139 A | 7/1992 | Brown et al. | 424/450 |
| 5,232,692 A | 8/1993 | Isenberg et al. | 424/78.04 |
| 5,246,708 A | 9/1993 | von Borstel et al. | 424/450 |
| 5,290,540 A | 3/1994 | Prince et al. | 424/45 |
| 5,456,923 A | 10/1995 | Nakamichi et al. | 424/489 |
| 5,552,158 A | 9/1996 | Evans et al. | 424/450 |
| 5,863,556 A * | 1/1999 | Ruckert et al. | 424/450 |
| 5,942,245 A | 8/1999 | Katinger et al. | |

FOREIGN PATENT DOCUMENTS

| | | |
|---|---|---|
| EP | 0260241 | 3/1988 |
| EP | 0317405 | 5/1989 |
| EP | 0407028 | 1/1991 |
| EP | 0509338 | 10/1992 |
| EP | 0613685 | 9/1994 |
| EP | 06390373 A1 * | 2/1995 |
| EP | 1013269 | 6/2000 |
| JP | 63126820 | 5/1988 |
| JP | 2204413 | 8/1990 |
| JP | 7145081 | 6/1995 |
| WO | WO 85/00112 * | 1/1985 |
| WO | 8809165 | 12/1988 |
| WO | 9011781 | 10/1990 |
| WO | 9324165 | 12/1993 |
| WO | 9414490 | 7/1994 |
| WO | 9422876 | 12/1994 |
| WO | 9614083 | 5/1996 |
| WO | 9960998 | 12/1999 |
| WO | 9960999 | 12/1999 |
| WO | 9961003 | 12/1999 |

OTHER PUBLICATIONS

Hardman et al. "Goodman & Gilman's The Pharmacological Basis of Therapeutics" (9th ed, 1996) p. 51 and 57-58.*
Raab W . Dermatologica, (1976) 152 Suppl 1, 67-79.*
Abstract EP 0613685 (English), Sep. 7, 1994.
Abstract EP 0509338 (English), Oct. 21, 1992.
Janine F. Bridges, et al., "*The Uptake of Liposome-Entrapped I-Labelled-Poly (Vinyl Pyrrolidone) By Rat Jejunum In-Vitro*," Biochemica et Biophysica Acta, 544 (1978) 448-451.
Peter M. Vogt, et al., "*Polyvinyl pyrrolidone-iodine Lipsome Hydrogel Improves Epithelialization By Combing Moisture And Antisepsis. A New Concept In Wound Therapy*," Wound Repair and Regeneration vol. 9 No. 2 p. 116-122, Mar.-Apr. 2001.

(Continued)

*Primary Examiner*—Sreeni Padmanabhan
*Assistant Examiner*—Shobha Kantamneni
(74) *Attorney, Agent, or Firm*—Jones Day

(57) ABSTRACT

Disclosed in certain embodiments is a method of treating infections of an interior part of the human or animal body, comprising administering to said interior body part, a pharmaceutical preparation comprising a particulate carrier and an effective amount of an agent selected from the group consisting of an antiseptic agent, a wound-healing promoting agent and a combination thereof, to treat an infection at said interior body part.

24 Claims, No Drawings

OTHER PUBLICATIONS

Karen Reimer, et al., "*An Innovative Topical Drug Formulation for Wound Healing And Infection Treatment: In-Vitro and In-Vivo Investigations of a Povidone-Iodine Liposome Hydrogel,*" Dermatology 2000, 201: 235-241.

Janny Liautard, et al., "*Encapsulation of Drugs Into Large Unilamellar Lipsomes Prepared by an Extemporaneous Method,*" J. Microencapsulation, 1991, vol. 8, No. 3, 381-389.

Brian E. Gilbert, et al., "*Aerosolized Liposomal Amphotericin B for Treatment of Pulmonary and Systemic Cryptococcus neoformans Infections in Mice,*" Antimicrobial Agents and Chemotherapy, Jul. 1992, p. 1466-1471.

Brian E. Gilbert, et al., "*Aerosolized Liposomal Amphotericin B for Treatment of Pulmonary and Systemic Cryptococcus neoformans Infections in Mice,*" Antimicrobial Agents and Chemotherapy, Jul. 1992, p. 1466-1471.

P. Würzler, et al., "*Virucidal and Chlamudicidal Activites of Povidone-Iodine (PVP-1) Lipsomes,*" Clin Microbial Inf 5(suppl 3) 136 (1990) 9th European Conference on Clin Microbiology and Infectious Diseases, Berlin, Mar. 1999.

Bernhard Müllinger, et al., "*Coated Drug Droplets Allow Individual Dosimetry,*" Respiratory Drug Delivery VI, Hilton Head, S.C. May 3-7, 1998, p. 385-387.

James F. Fitzgerald, et al., "*Novel Coating For Improved Pulmonary Drug Delivery,*" U. Of Florida Office of Graduate Research, Technology and Education, VF#1887, Jan. 15, 1998 (ABSTRACT).

David A. Edwards, et al., "*Large Porous Particles for Pulmonary Drug Delivery,*" Science, vol. 276, Jun. 20, 1997, p. 1868-1871.

H. Schreier, et al., "*Formulation and in-vitro performance of liposome powder aerosols,*" S.T.P. Pharma Sciences 4(1) 38-44, 1994.

Hans Schreier, et al., "*Pulmonary delivery of liposomes,*" Journal of Controlled Release, 24 (1993) 209-223.

Abstract JP 2204413 and JP 63126820 (English), 1988, May 30, 1998.

Xiaonan Cia, 1994, "The Clinical Use and Dosage Form of Iodophors", Bulletin of the Medical School of Shantou University (2):77-89 (in Chinese and English).

Ganzer et al., 2001, Arthroskopie 14:31-44.

* cited by examiner

PREPARATIONS FOR THE APPLICATION OF ANTI-INFLAMMATORY AGENTS

The invention concerns preparations for the application of agents with anti-inflammatory, especially antiseptic and/or wound healing promoting properties, to the interior of the human or animal body. The preparations are specifically applied to bones, organs, joints, muscle tissue, mucous membranes and mucosa-like unkeratinized epithelial tissues forming interior body parts of humans and animals. Especially, the invention concerns the prevention or treatment of infections in joints such as the knee, the hip joint, the shoulder joint and the elbow.

Furthermore, the invention concerns a method of preventing or treating infections by applying a pharmaceutical preparation.

A plurality of different antibiotic and antiseptic agents are known for the topical treatment of infectious maladies. A decisive disadvantage of antibiotic agents is that the infecting bacteria show primary resistances, and can acquire secondary resistances, against these agents. Further, antibiotics quite often lead to patient sensibilisation. The use of e.g. halogen-releasing antiseptics such as povidone iodine, also known as polyvidone iodine or PVP-iodine, i.e. the poly(1-vinyl-2-pyrrolidin-2-one)-iodine complex, can prevent resistances. Antiseptic agents are also much more rarely allergenic as compared to antibiotics.

A plurality of different antibiotic and antiseptic agents are known for the topical treatment of infectious maladies. A decisive disadvantage of antibiotic agents is that the infecting bacteria show primary resistances, and can acquire secondary resistances, against these agents. Further, antibiotics quite often lead to patient sensibilisation. The use of e.g. halogen-releasing antiseptics such as povidone iodine, also known as polyvidone iodine or PVP-iodine, i.e. the poly(1-vinyl-2-pyrrolidin-2-one)-iodine complex, can prevent resistances. Antiseptic agents are also much more rarely allergenic as compared to antibiotics.

At present, infectious diseases of the interior body parts are generally treated with antibiotics. This leads to the complications which are known to the skilled person. For example, patients suffering from chronical inflammation of joints, such as the knee or elbow, are often treated with antibiotics in order to alleviate the symptoms. However, this often merely leads to resistances of the bacteria which are responsible for the symptoms. Many diseases are caused by viruses and against these, antibiotics are not effective. Such patients are not cured from the infections.

The use of antiseptic and/or wound-healing promoting agents for external application to humans and animals is disclosed in our earlier patent EP 0 639 373. Specifically, liposome preparations of PVP-iodine are shown therein to be topically applicable to the external parts of the eye. These preparations generally take the form of a cream, an ointment, a lotion, a gel or a drop formulation.

Liposomes are well-known drug carriers and therefore the application of medicaments in liposomal form has been subject of investigation for quite some time. An overview concerning (pulmonary) delivery of liposome encapsulated drugs (in asthma therapy) is provided by the review "Pulmonary delivery of liposomes" (H. Schreier, in "Journal of Controlled Release", 24, 1993, p. 209-223). The physicochemical characterization of liposome aerosols and also their therapeutic applications to the respiratory tract are shown therein. Drugs that have been investigated for pulmonary delivery via liposomes include, e.g. anti-cancer agents, peptides, enzymes, anti-asthmatic and anti-allergic compounds and, as mentioned above, also antibiotics. The formulation of liposome aerosols or liposome powder aerosols using, for example a dry powder inhaler has also been described by H. Schreier in "Formulation and in vitro performance of liposome powder aerosols" (S.T.P. Pharma Sciences 4, 1994, p. 38-44).

Although, especially in the lower respiratory tract or for external application, some attention has been paid for quite some time to liposomes as drug carriers, there appears to be no prior art relating to liposomes and other particulates as carriers of antiseptic or wound-healing promoting agents for applications in the interior of the body, especially in joints.

In fact, there appears to be a marked reluctance in the art, to apply disinfectants to interior parts of the body, except maybe in extreme cases of life-threatening septical complications. Generally, antibiotic preparations appear to be preferred, even in view of their above-discussed disadvantages.

An object of the instant invention is to provide a well tolerated, easily applicable antiseptic and/or wound-healing promoting preparation, which provides protracted release and protracted topical effect of the active agent in the body interior, especially in joints, such as the knee, the hip joint, the elbow, the shoulder joint etc.

According to the invention this object is attained in that the preparation comprises at least one antiseptic and/or wound healing promoting agent in the form of a particulate carrier preparation, as defined in independent claim 1.

The invention further comprises a method of treating interior parts of the body, in humans and animals, as defined in independent claim 19.

The dependent claims define further advantageous embodiments of the invention.

The invention is premised on the surprising fact that particulate carriers, especially liposomes, are highly suited as carriers for antiseptic agents, especially for povidone iodine, and for agents promoting the healing of wounds, for application to interior body parts, especially joints.

The preparations according to this invention permit protracted release of the agent or agents, and provide an extended and topical activity at the desired locus of action by interaction with cell surfaces.

In the context of the invention, the body interior is considered to broadly include those parts of the body which are enclosed by the skin, excluding the external skin areas and the cavities which are freely accessible from the outside, basically those leading from the mouth through the gastro-intestinal tract to the organs of excretion, and those leading from the nose into the lung.

In the context of the invention, anti-inflammatory agents are understood to include antiseptic agents, antibiotic agents, corticosteroids, and wound-healing agents, as defined below.

In the context of this invention, antiseptic agents are understood to include those disinfecting agents which are pharmaceutically acceptable and suitable for the treatment of the interior of the human or animal body to the extent that they can be formulated in accordance with the invention.

More specifically, antiseptic agents include inter alia oxygen- and halogen-releasing compounds; metal compounds, e.g. silver and mercury compounds; organic disinfectants including inter alia formaldehyde-releasing compounds, alcohols, phenols including alkyl- and arylphenols as well as halogenated phenols, quinolines and acridines, hexahydropyrimidines, quaternary ammonium compounds and iminium salts, and guanidines.

Wound-healing agents comprise agents promoting granulation and epithelization such as dexpanthenol, allantoines, azulenes, tannines, and vitamine B-type compounds.

The invention is, another aspect, based on a further surprising and unexpected fact. It is well known in the art that the formation of new body tissues may cause problems. Thus, it is known that body tissue repair may be accompanied by the formation of scar tissue, which can be functionally and/or cosmetically harmful, or at least undesirable. Hyperkeratosis and the uncontrolled proliferation of tissue may cause serious harm, leading to dysfunctions, and may of course also be cosmetically undesirable. After infections and inflammations, re-growing or healing tissue may cause neoplasms and intergrowth. It is thus well known in the art that in the curing of diseases, proper remodelling of tissue is not only desirable, but in fact necessary.

It has now been surprisingly found that the use of anti-inflammatory agents, singly or in combination with other such agents, leads to markedly less formation of undesirable body tissue in the course of tissue repair and other tissue growth processes. Thus, the formation of scar tissues is reduced, in skin but also in mucosa and in other tissues, such as muscle or inner organ tissues. Hyperkeratosis may be entirely suppressed, and intergrowth, or neoplasm formation in the curing of infective diseases is also highly reduced.

One object achieved by the invention is therefore concerned with improved tissue repair in the body. The invention achieves this by the application of anti-inflammatory agents, in the form of a particulate carrier preparation as defined in the independent claims.

The antiseptic or wound-healing preparation will generally be administered to the interior body part to be treated by invasive methods, especially by injection of the particulate carrier preparation, or by application of the respective preparation after a surgical step providing access to the locus of treatment. For example, a liposome preparation can be made by loading liposomes with PVP iodine in a conventional procedure. The nature or constitution of the liposomes are not critical. The liposome preparation as, for example, described in EP 0 639 373 can be administered by injection. The disclosure of EP 0 639 373 is incorporated by reference.

The preparations according to this invention apparently do not only contain the active agent, like povidone iodine, encapsulated in the particulate carrier, especially in liposomes. It seems that there is also some amount of agent which is not contained inside the carrier. The preparations according to the invention often show a marked initial effect which is observed in addition to the slower, protracted release of the active agent from the carrier. This effect is especially observed where the carrier comprises liposomes. Without wishing to be bound to any theoretical explanation, it is presently assumed that in addition to active agent encapsulated inside the liposomes, some active agent is present outside of the liposomes, and probably losely bound to the outer surfaces of the liposomes. This could be due to association of active agent molecules with the liposomal membrane, or it could be due to active agent molecules forming a layer on the liposomal surface, which layer partly or even fully coats the liposome externally. The type and amount of this initial agent effect can e.g. be influenced by choice of the concentration parameters.

Anti-inflammatory preparations according to this invention thus make it possible to achieve effects which cannot be provided by customary preparations.

Preferred antiseptic agents comprise the well-known pharmaceutical substances providing fast effect, a broad range of activity, low systemic toxicity and good tissue compatibility. They can e.g. be selected from the group comprising metal compounds, phenolic compounds, detergents, iodine and iodine complexes. A specifically preferred antiseptic agent is povidone iodine.

Preferred agents promoting the healing of wounds comprise substances which have been described in the literature for such application. Preferred such agents include substances known to promote epithelisation. These include vitamins, specifically from the vitamin B group, allantoin, some azulenes etc.

In preferred embodiments, the invention's preparations containing antiseptic and/or wound-healing promoting agents can comprise further agents such as anaesthetic agents. Inventive preparations can also contain customary further agents, including adjuvants and additives, antioxidants, conserving agents or consistency-forming agents such as viscosity adjusting additives, emulgators etc.

The amphiphilic substances generally known in prior art to form liposome membranes can be employed in the context of the invention as long as they are pharmaceutically acceptable for the intended application. Presently, liposome forming systems comprising lecithine are preferred. Such systems can comprise hydrogenated soy bean lecithine besides cholesterol and disodium succinate-hexahydrate; it is presently specifically preferred to use hydrogenated soy bean lecithine as the sole membrane forming agent.

The known prior art methods for forming liposome structures can generally be used in the context of the invention. Broadly, these methods comprise mechanical agitation of a suitable mixture containing the membrane forming substance and water or an aqueous solution. Filtration through suitable membranes is preferred in forming a substantially uniform liposome size.

The size of the liposomes can vary over a broad range, generally from about 1 to about 20,000 nm. Liposomes with diameters between 50 and 4,000 nm are preferred and liposomes of up to approximately 1,000 nm diameter are presently most preferred. For solutions, smaller average diameters may be more suitable.

Where alternative particulate carriers are used, they are generally prepared as known in the art. Thus, microspheres which are used to deliver a very wide range of therapeutic or cosmetic agents, are made as described for example in WO 95/15118.

Nanoparticles may in some cases be used, provided that they can be loaded with a sufficient amount of active agent and can be administered according to this invention. They can be prepared according to the methods known in the art, as e.g. described by Heyder (GSF München) in "Drugs delivered to the lung, Abstracts IV, Hilton Head Island Conference, May 1998.

Methods using a pulse laser deposition (PLD) apparatus and a polymeric target to apply coatings to drug powders in a short non-aqueous process are also suitable for the formation of particulate preparations according to this invention. These have e.g. been described by Talton et al., "Novel Coating Method for Improved Dry Delivery", Univ. of Florida UF 1887 (1998).

A further suitable delivery system employs "Large-Porous Particles" as disclosed by David A. Edwards et al. in "Large Porous Particles for Pulmonary Drug Delivery" (Science, 20 Jun. 1997, Vol. 276, p. 1868-1871).

Generally, the concentrations in the preparation, particle sizes, active agent loadings etc. will be selected for such alternative carriers to correspond basically to the parameters discussed herein with respect to liposome preparations. Selecting and providing such parameter based inter alia on straightforward experimentation, is well within the skill of an ordinary worker experienced in this art.

A presently highly preferred use of the inventive liposome preparations is in the local treatment of infections of joints, such as the knee, hip, elbow and shoulder joints, especially when the liposome preparations contain povidone iodine. Also in this indication, the inventive antiseptic preparations, especially those containing PVP iodine, have the great advantage of not causing resistances and lead to much less allergic reactions, while permitting a very cost-efficient therapy with a broad spectrum of effect. A povidone iodine liposome preparation according to this invention is e.g. effective against viruses. This effect is not provided by antibiotic agents. Further, a liposome preparation of a microbicidal agent such as povidone iodine provides protracted release of the agent from liposomes. This leads to extended effect of the antimicrobial substance, and thus less frequent application, as compared with the customary antiseptic solution preparations.

The present invention is also useful in the treatment of infectious diseases or for alleviation of diseases such as HIV infections which are accompanied by opportunistic infections. Also patients having a suppressed immune system, for example, after organ transplants, can be treated according to the invention. In particular, acute and chronical bronchitis, pneumonia, bronchiectasia, cystic fibrosis, diphtheria, tuberculosis can be treated with the povidone iodine preparation according to the invention.

Another highly preferred use is in tissue repair, especially in functional and cosmetic tissue remodelling.

Preparations according to this invention can take a variety of forms, including solutions, dispersions, sprays and gels. Solid forms may sometimes be useful or even advantageous, but are generally less preferred than liquid forms.

Generally, the amount of active agents in an inventive preparation will be determined by the desired effect, on the one hand, and the carrying capacity of the carrier preparation for the agent, on the other hand.

Broadly, a solution or dispersion of active agent in an inventive carrier preparation can range in concentration between the lower limit of effectiveness of the agent and the solubility or dispersability limit of the agent in the respective solvent, dispersant, spray or gel.

More specifically, for an antiseptic such as povidone iodine, a solution or dispersion in an inventive carrier preparation, especially where the carrier is a liposome preparation, can contain between 0.1 and 10 g of agent in 100 g of preparation. Such a preparation will then typically contain between 1 and 5 g of liposome membrane forming substance, especially lecithine, per 100 g of preparation.

Especially preferred is an injectable preparation, which comprises up to 10% povidone iodine (at 10% iodine content) in a physiological saline liposome dispersion.

The features and advantages of this invention will become notable in more detail from the ensuing description of preferred embodiments. In these embodiments which include a best mode, povidone iodine is exemplified as an antiseptic agent and liposomes are chosen as the carrier. This should, however, not be construed as a restriction of this invention to antiseptic agents or, among antiseptic agents, to povidone iodine, and/or to liposomes as the carrier, although such preparations are specifically preferred.

One preferred method for producing the invention's liposomes can generally be described as follows:

The lipid membrane-forming components, e.g. lecithine, are dissolved in a suitable solvent such as chloroform or a 2:1 mixture of methanol and chloroform and are filtered under sterile conditions. Then, a lipid film is produced on a sterile high surface substrate, such as glass beads, by controlled evaporation of the solvent. In some cases, it can be quite sufficient to form the film on the inner surface of the vessel used in evaporating the solvent, without using a specific substrate to increase the surface.

An aqueous system is prepared from electrolyte components and the (one or more) active agents to be incorporated in the liposome preparation. Such an aqueous system can e.g. comprise 10 mmol/l sodium hydrogen phosphate and 0.9% sodium chloride, at ph 7.4; the aqueous system will further comprise at least the desired amount of the active agent, which in the embodiment examples is povidone iodide. Often, the aqueous system will comprise an excess amount of agent or agents.

The liposomes are generally formed by agitating said aqueous system in the presence of said film formed by the lipid components. At this stage, further additives can be added to improve liposome formation; e.g. sodium cholate can be added. Liposome formation can also be influenced by mechanical action such as pressure filtration through e.g. polycarbonate membranes, or centrifuging. Generally, the raw liposome dispersion will be washed, e.g. with electrolyte solution as used in preparing the above-described solution of the active agent.

When liposomes with the required size distribution have been obtained and washed, they can be redispersed in an electrolyte solution as already described, often also comprising sugars such as saccharose or a suitable sugar substitute. The dispersion can be freeze-dried, and it can be lyophilysed. It can, prior to use, be reconstituted by addition of water and suitable mechanical agitation at the transition temperature of the lipid component, which for hydrogenated soy bean lecithine is e.g. 55° C.

In the following Examples, hydrogenated soy bean lecithine (EPIKURON™ 200 SH obtainable from Lukas Meyer, Germany or PHOSPOLIPON™ 90H obtainable from Nattermann Phospholipid GmbH, Germany) was used. However, other pharmaceutically acceptable liposome membrane forming substances can be used instead, and the person skilled in the art will find it easy to select suitable alternative liposome forming systems from what is described in prior art.

EMBODIMENT EXAMPLE I

In a 1000 ml glass flask, provided with glass beads for increased surface, 51.9 mg cholesterol and 213 mg hydrogenated soy bean lecithine were dissolved in a sufficient amount of a mixture of methanol and chloroform in a 2:1 ratio. The solvent was then evaporated under a vacuum until a film was formed on the inner surface of the flask and on the glass beads.

2.4 g PVP iodine (containing about 10% available iodine) were separately dissolved in 12 ml water.

Again in a separate vessel, 8.77 g sodium chloride and 1.78 g $Na_2HPO_4.2H_2O$ were dissolved in 400 ml water. Further water was added up to a total volume of 980 ml, and then, approximately 12 ml 1N hydrochloric acid were added to adjust pH to 7.4. This solution was then topped up with water to exactly 1000 ml.

In a fourth vessel, 900 mg saccharose and 57 mg disodium succinate were dissolved in 12 ml water.

The PVP iodine solution was then added to the lipid film in the flask and the mixture was shaken until the film dissolved. The resulting liposome formulation was seperated from the hydrated lipids in the flask. The product was centrifuged and the supernatant liquid was discarded. The saccharose solution was added ad 12 ml and the product was again centrifuged. Afterwards the supernatant liquid was again discarded. At this stage, a further washing step, using the saccharose solution or the sodium chloride buffer solution could be used.

After the last centrifugation step and discarding of the supernatant, sodium chloride buffer solution was added ad 12 ml, and the liposomes were homogenously distributed therein. The product was then distributed into vials each containing 2 ml liposome dispersion, and the vials were then subjected to a freeze-drying step.

After the freeze-drying, each vial comprised about 40 mg solids.

The method of Embodiment Example I has a minor disadvantage in that the PVP iodine solution used, due to the high percentage of solids, is rather viscous and thus more difficult to handle.

EMBODIMENT EXAMPLE II

In a 2000 ml flask provided with glass beads to increase surface, 173 mg hydrogenated soy bean lecithine and 90 mg disodium succinate were dissolved in approximately 60 ml of a methanol/chloroform mix in a 2:1 ratio. The solvent was removed under vacuum until a film was formed.

4 g PVP iodine (10% available iodine) were dissolved in 40 ml of the sodium chloride buffer solution described in Embodiment Example I, and were added to the lipid film in the flask. The flask was then shaken until the film dissolved and liposomes were formed.

The product was centrifuged and the supernatant liquid was discarded.

To the thus produced liposome pellet, further sodium chloride buffer solution was added ad 40 ml, and the centrifuging step was repeated. The supernatant was again discarded. At this stage, this washing step could be repeated where necessary.

After the final centrifuging and decanting step, sodium chloride buffer solution was again added to the precipitated liposomes ad 40 ml. The homogenous dispersion was then distributed into vials, each vial containing about 2 ml liposome dispersion, and the vials were then subjected to a freeze-drying step. This produced approximately 200 mg freeze-dried solids per vial.

From the freeze-dried solids of Examples I and II, further preparations were made as described in subsequent Embodiment Examples and Test Reports.

Like that of Embodiment Example I, the above-described method uses a hydrating step after film formation in the presence of organic solvents and aims at inclusion rates of 5 bis 15%. These methods generally produce rather large and often multi-lamellar liposomes.

The above-described methods can be modified by a high pressure filtering step through a suitable membrane such as a polycarbonate membrane after the raw liposomes have been formed or after any of the subsequent washing steps or directly by using high pressure homogenisation. This produces much smaller, unilamellar liposomes at increased amounts of encapsulated agent.

Instead of high pressure homogenisation, other prior art methods known to provide small uniform sized liposomes can be employed.

EMBODIMENT EXAMPLE III

An injectable dispersion was prepared from 10 g hydrogenated soy bean lecithine/PVP iodine liposomes as described in Embodiment Example II; these were mixed with physiological saline ad 100 g.

Further modifications of the above-described embodiments are envisaged.

Thus, the dispersion of Embodiment Example III can have an additional content of an agent known to promote the healing of wounds, such as allantoin. Such an agent will be added in a pharmaceutically useful concentration, in the case of allantoin in the range of 0.1 to 0.5 g, per 100 g of dispersion. The wound-healing agent can be incorporated in the saline, in which case it will largely be outside the liposomes. It can, however, be partly or mostly incorporated in the liposomes, in which case it will be added at a corresponding suitable stage of the liposome preparation method.

It is also possible to prepare embodiments similar to the above described ones, which comprise an agent capable of promoting the healing of wounds instead of, and not in addition to, the antiseptic agent as e.g. povidone iodine disclosed in the above Embodiment Examples. Presently, it is however preferred to use a wound healing promoting agent (if at all) in addition to an antiseptic agent.

Test I

This was an in-vitro-test of the bactericidal effect provided by an inventive povidone iodine liposome preparation. The test was based on the quantitative suspension test as described in "Richtlinien der Deutschen Gesellschaft für Hygiene und Mikrobiologie", 1989. In this test, the bactericidal agent is used to kill *staphylococcus aureus* (ATCC 29213), a major problem in hospital hygiene.

The liposome preparation used was that of Embodiment Example 1. At different contact times between 1 und 120 minutes, the minimum concentration of the preparation in water was determined which was capable of killing the staphilococci.

The results are shown in Table 1.

TABLE I

| Contract Time (Minutes) | Bactericidal Concentration |
| --- | --- |
| 1, 2, 3, 4 | $\geq 0.060\%$ |
| 5, 30, 60 | $\geq 0.015\%$ |
| 120 | $\geq 0.007\%$ |

The results show that at short contact times (between 1 and 4 minutes) the bactericidal concentration is as low as 0.06% and that at long contact times (120 minutes) the bactericidal concentration can be as low as 0.007%.

Test II

The virucidal and chlamydicidal activity of liposomal PVP-iodine has been studied, in cell cultures, by Wutzler et al., 9th European Congress for Clinic Microbiology and Infection Diseases, Berlin, March 1999. In cell cultures, liposomal PVP-iodine is highly effective against herpes simplex virus type 1 and adenovirus type 8, while the long-term cytotoxicity experiments indicated that the liposomal form is better tolerated than aqueous PVP-iodine by the majority of cell lines tested. PVP-iodine in liposomal form is not genotoxic.

Test III

A 3% PVP-iodine hydrogel liposomal preparation was compared with a 3% PVP-iodine ointment, where the active agent was not in liposomal form. The agent was applied to standardized in vitro cultures of rat skin and peritoneal explants, as a screening for tissue compatibility of skin and wound antiinfectives.

The growth rate of the cultured explants was studied after 30 minutes exposure and incubation with a test substance.

Again, the substantially better toleration of the liposomal preparation was clearly shown in the results, in terms of peritoneum growth rate and skin growth rate.

With the ointment, the peritoneum growth rate reached 85%, and the skin growth rate reached 90%; with the liposomal hydrogel formulation, the peritoneum growth rate was 96%, and the skin growth rate was 108%; these values are to be compared with 100% values in a control test using Ringer's solution as the agent.

Test IV

In an unpublished study, the effects of povidone iodine in non-liposomal form was studied on adult articular cartilage.

Sesamoid bones were dissected within 2-4 h after slaughter from bovine metacarpo-phalangeal joints of adult animals under aseptic conditions. The cartilage from sesamoid bones of a particular animal is uniform with respect to glycosaminoglycan synthesis, glycosaminoglycan content, and proteoglycan composition. Each experimental group consisted of eight sesamoid bones from the same animal. The sesamoid bones were washed in 10 ml cold sterile Ringer's solution for 10 min, incubated respectively in 10 ml of sterile Ringer's solution (control), PVP-iodine, or PVP-iodine dilutions with Ringer's solution (1:10, 1:100, or 1:1000) at 37° C. for 10 min in a humidified atmosphere of 5% $CO_2$ in air, and subsequently washed again for 5×5 min in 10 ml Ringer's solution in each case. After incubation of each pre-treated sesamoid bone for 24 h at 37° C. in 10 ml Ham F-12 medium, supplemented with antibiotics, cartilage plugs of 2.8 mm in diameter were carefully removed and extracted thereafter in a stepwise manner. The culture media of sesamoid bones and extracts of cartilage plugs were used for the quantitative and qualitative characterization of proteoglycans and COMP (cartilage oligomeric matrix protein), because an increased release of fragments of these cartilage matrix constituents equals to a catabolic pathway.

10 min treatment of sesamoid bones with undiluted or diluted PVP-iodine induces no increased proteolytic fragmentation of investigated cartilage matrix constituents, compared with control experiments in Ringer's solution. That means there were no destructive activities in cartilage after the exposure to PVP-iodine.

This shows the desired tolerance of joint cartilage material to PVP-iodine even in non-liposomal form. As is known from the above reported other tests, liposomal preparations are even better tolerated than non-liposomal PVP-iodine preparations. Thus, the inventive liposomal or otherwise "carried" agent preparations would be expected to be evenly better tolerated as compared to the "uncarried" corresponding agent preparations.

The invention claimed is:

1. A method of treating an infection of an interior part of an animal, comprising administering to an interior part of an animal in need thereof an amount of liposomes sufficient to treat the infection, said liposomes containing povidone iodine.

2. The method of claim 1, wherein the liposomes further contain dexpanthenol, allatonin, azulene, tannin, a vitamin B compound, or a combination thereof.

3. The method of claim 1, wherein the liposomes further contain an anesthetic agent.

4. The method of claim 1, wherein the liposomes further contain a conserving agent, an antioxidant, or a consistency-forming agent.

5. The method of claim 1, wherein the infection is an opportunistic infection.

6. The method of claim 1, wherein said interior part is selected from the group consisting of a bone, an organ, a joint and muscle tissue.

7. The method of claim 1, wherein said interior part is a joint.

8. The method of claim 7, wherein said joint is selected from the group consisting of the knee joint, the hip joint, the shoulder joint and the elbow joint.

9. The method of claim 1, wherein the liposomes have a diameter in the range from about 1 nm to about 20,000 nm.

10. The method of claim 9, wherein the liposomes have a diameter in the range from about 50 nm to about 4000 nm.

11. The method of claim 1, wherein the liposomes further contain a pharmaceutically acceptable additive.

12. The method of claim 1, wherein the liposomes are in the form of a powder, a spray, an emulsion or a dispersion.

13. The method of claim 1, wherein the liposomes further contain a corticosteroid.

14. The method of claim 1, wherein the liposomes further contain an antibiotic.

15. The method of claim 1, wherein the infection is a bacterial, fungal, or viral infection.

16. The method of claim 1, wherein the animal is a human.

17. The method of claim 1, wherein said liposomes contain between 0.1 to 10%, by weight, povidone iodine.

18. The method of claim 1, wherein said liposomes comprise a liposome membrane forming substance that is present in an amount between 1 to 5%, by weight, of the liposomes.

19. The method of claim 1, wherein said liposomes are lecithin liposomes.

20. A method of treating an infection of a bone, comprising administering to the bone in an animal in need thereof an amount of liposomes sufficient to treat the infection, said liposomes containing povidone iodine.

21. A method of treating an infection of an organ, comprising administering internally to an organ in an animal in need thereof an amount of liposomes sufficient to treat the infection, said liposomes containing povidone iodine.

22. A method of treating an infection of muscle tissue, comprising administering to muscle tissue in an animal in need thereof an amount of liposomes sufficient to treat the infection, said liposomes containing povidone iodine.

23. A method of treating an infection of a joint, comprising administering to a joint in an animal in need thereof an amount of liposomes sufficient to treat the infection, said liposomes containing povidone iodine.

24. The method of claim 23, wherein said joint is selected from the group consisting of the knee joint, the hip joint, the shoulder joint and the elbow joint.

* * * * *